United States Patent [19]
Wollmann et al.

[11] 3,979,385
[45] Sept. 7, 1976

[54] 1-AMINOALKANE-1,1-DIPHOSPHONIC ACIDS AND THEIR SALTS

[75] Inventors: Klaus Wollmann; Walter Ploger, both of Hilden; Karl-Heinz Worms, Dusseldorf-Holthausen, all of Germany

[73] Assignee: Henkel & Cie G.m.b.H., Dusseldorf-Holthausen, Germany

[22] Filed: May 31, 1974

[21] Appl. No.: 475,207

Related U.S. Application Data

[62] Division of Ser. No. 90,454, Nov. 17, 1970, Pat. No. 3,846,420.

[30] Foreign Application Priority Data

Nov. 19, 1969  Germany............................ 1958123

[52] U.S. Cl............................. 260/247; 260/293.51
[51] Int. Cl.² ........................................ C07D 295/04
[58] Field of Search.......... 260/247, 293.51, 326.61, 260/502.5

[56] References Cited
UNITED STATES PATENTS

| | | | |
|---|---|---|---|
| 3,488,419 | 1/1970 | McCune et al. | 424/49 |
| 3,617,343 | 11/1971 | Kandler et al. | 260/502.5 |
| 3,668,138 | 6/1972 | Hoover et al. | 260/502.5 |
| 3,792,084 | 2/1974 | Quinlan | 260/247 |
| 3,846,482 | 11/1974 | Kerst | 260/502.5 |

*Primary Examiner*—Lorraine A. Weinberger
*Assistant Examiner*—Michael Shippen
*Attorney, Agent, or Firm*—Hammond & Littell

[57] ABSTRACT

A process for the production of 1-aminoalkane-1,1-diphosphonates of the formula

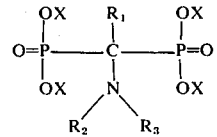

wherein $R_1$ is a member selected from the group consisting of hydrogen, lower alkyl and phenyl, $R_2$ and $R_3$ are members selected from the group consisting of hydrogen, alkyl having 1 to 22 carbon atoms, cycloalkyl having 5 to 6 carbon atoms, phenyl, alkylphenyl having 7 to 18 carbon atoms, phenylalkyl having 7 to 18 carbon atoms and together with the nitrogen atom, piperidino, pyrrolidino and morpholino, and X is a member selected from the group consisting of hydrogen, alkali metal, ammonium, pyridinium, guanidinium and mono-, di-, and tri-lower-alkanolammonium with the proviso that at least one of $R_1$, $R_2$ and $R_3$ is other than hydrogen, which consists essentially in reacting a phosphorus trihalide selected from the group consisting of phosphosus trichloride and phosphorus tribromide with a monocarboxylic acid amide of the formula

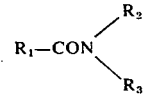

wherein the molecular weight of said carboxylic acid amide is over 46 and $R_1$, $R_2$ and $R_3$ have the above assigned meanings, at a temperature of from 0° to 75°C, subjecting the resultant reaction product to hydrolysis, and recovering said 1-aminoalkane-1,1-diphosphonates. The 1-aminoalkane-1,1-diphosphonates, some of which are novel, are capable of forming complexes with heavy metals.

2 Claims, No Drawings

1-AMINOALKANE-1,1-DIPHOSPHONIC ACIDS AND THEIR SALTS

This is a division of Ser. No. 90,454, filed Nov. 17, 1970, now U.S. Pat. No. 3,846,420.

THE PRIOR ART

The preparation of 1-aminoalkane-1,1-diphosphonic acids by reaction of alkylnitriles with $PBr_3$ or $PCl_3$ is known, but satisfactory yields are only obtained with $PBr_3$. The preparation of compounds in which the amino group is substituted, for example by alkyl residues is, however, not possible by this process. The preparation of N,N-dimethyl-1-aminomethane-1,1-diphosphonic acid tetraethyl ester by reaction of dimethyl formamide diacetal with diethyl phosphite is also known. This process is complicated, all the more so as the esters still have to be converted into the free acids.

OBJECTS OF THE INVENTION

An object of the present invention is the development of a process for the production of substituted 1-aminoalkane-1,1-diphosphonates.

Another object of the invention is the development of a process for the production of 1-aminoalkane-1,1-diphosphonates of the formula

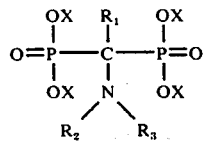

wherein $R_1$ is a member selected from the group consisting of hydrogen, lower alkyl and phenyl, $R_2$ and $R_3$ are members selected from the group consisting of hydrogen, alkyl having 1 to 22 carbon atoms, cycloalkyl having 5 to 6 carbon atoms, phenyl, alkylphenyl having 7 to 18 carbon atoms, phenylalkyl having 7 to 18 carbon atoms and together with the nitrogen atom, piperidino, pyrrolidino and morpholino, and X is a member selected from the group consisting of hydrogen, alkali metal, ammonium, pyridinium, guanidinium and mono-, di-, and tri-lower-alkanol-ammonium, with the proviso that at least one of $R_1$, $R_2$ and $R_3$ is other than hydrogen, which consists essentially in reacting a phosphorus trihalide selected from the group consisting of phosphorus trichloride and phosphorus tribromide with a monocarboxylic acid amide of the formula

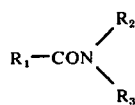

wherein the molecular weight of said carboxylic acid amide is over 46 and $R_1$, $R_2$ and $R_3$ have the above-assigned meanings, at a temperature of from 0° to 75°C, subjecting the resultant reaction product to hydrolysis, and recovering said 1-aminoalkane-1,1-diphosphonates.

A further object of the invention is the obtaining of 1-aminoalkane-1,1-diphosphonates selected from the group consisting of (1) aminomethane-1,1-diphosphonates of the formula

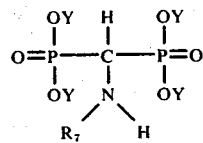

wherein $R_7$ represents a member selected from the group consisting of alkyl having from 1 to 18 carbon atoms, cyclohexyl, alkylphenyl having from 7 to 18 carbon atoms, and phenylalkyl having from 7 to 12 carbon atoms; (2) aminomethane-1,1-diphosphonates of the formula

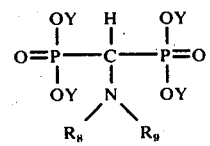

wherein $R_8$ and $R_9$ are members selected from the group consisting of alkyl having from 2 to 18 carbon atoms, and, together with the nitrogen atom, piperidino, pyrrolidino, and morpholino, and (3) 1-aminoethane-1,1-diphosphonates of the formula

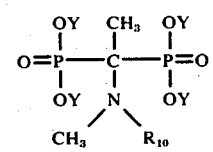

wherein $R_{10}$ represents a member selected from the group consisting of hydrogen and methyl; Y in each formula represents a member selected from the group consisting of hydrogen and alkali metal.

These and other objects of the invention will become more apparent as the description thereof proceeds.

DESCRIPTION OF THE INVENTION

It has now been found that 1-aminoalkane-1,1-diphosphonic acids, the amino group of which may possibly be substituted, may be easily prepared by using the process described below.

The present invention therefore provides a process for the preparation of 1-aminoalkane-1,1-diphosphonic acids and their salts comprising reacting a phosphorus trihalide with a monocarboxylic acid amide of the general formula

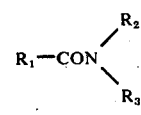

in which the molecular weight of the carboxylic acid amide is over 46 and $R_1$ represents a hydrogen atom or a lower alkyl residue or a phenyl residue, and $R_2$ and $R_3$ represent hydrogen atoms or organic residues, optionally forming a ring, and the reaction product is subsequently hydrolyzed and, if desired, any free acid converted into a salt.

Some of the 1,1-diphosphonic acids produced by the above process are novel and form a further feature of the present invention. Among the novel products are 1-aminoalkane-1,1-diphosphonates selected from the group consisting of 1. aminomethane-1,1-diphosphonates of the formula

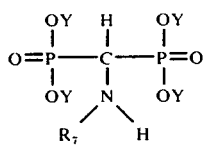

wherein $R_7$ represents a member selected from the group consisting of alkyl having from 1 to 18 carbon atoms, cyclohexyl, alkylphenyl having from 7 to 18 carbon atoms and phenylalkyl having from 7 to 12 carbon atoms, 2. aminomethane-1,1-diphosphonates of the formula

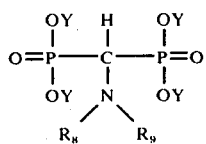

wherein $R_8$ and $R_9$ are members selected from the group consisting of alkyl having from 2 to 18 carbon atoms, and, together with the nitrogen atom, piperidino, pyrrolidino and morpholino, and 3. 1-aminoethane-1,1-diphosphonates of the formula

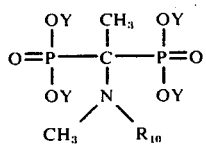

wherein $R_{10}$ represents a member selected from the group consisting of hydrogen and methyl; Y in each formula represents a member selected from the group consisting of hydrogen and alkali metal.

Acid amides suitable as starting substances are, for example, acetamide, propionamide, butyramide and benzamide. In these compounds, one or both hydrogen atoms of the amino group may be substituted by organic residues. Suitable organic residues are especially alkyl residues containing 1 to 18 carbon atoms, aralkyl, phenyl or cycloaliphatic residues, in particular, a cyclohexyl residue. The two organic residues may form a closed ring. $R_1$ and $R_2$ may then form a closed carbon chain, but may also contain hetero-atoms, especially oxygen or nitrogen. Suitable examples of these are the piperidine or morpholine rings. The substituents may also be the same or different. In addition to the already mentioned acid amides, correspondingly substituted formamides in particular may also be used as starting components.

In particular, therefore, the invention involves a process for the production of 1-aminoalkane-1,1-diphosphonates of the formula

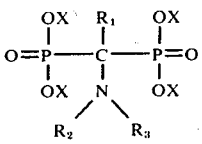

wherein $R_1$ is a member selected from the group consisting of hydrogen, lower alkyl and phenyl, $R_2$ and $R_3$ are members selected from the group consisting of hydrogen, alkyl having 1 to 22 carbon atoms, cycloalkyl having 5 to 6 carbon atoms, phenyl, alkylphenyl having 7 to 18 carbon atoms, phenylalkyl having 7 to 18 carbon atoms, and together with the nitrogen atom, piperidino, pyrrolidino and morpholino, and X is a member selected from the group consisting of hydrogen, alkali metal, ammonium, pyridinium, guanidinium and mono-, di- and tri-lower-alkanol-ammonium, with the proviso that at least one of $R_1$, $R_2$ and $R_3$ is other than hydrogen, which consists essentially in reacting a phosphorus trihalide selected from the group consisting of phosphorus trichloride and phosphorus tribromide with a monocarboxylic acid amide of the formula

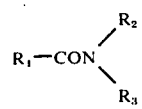

wherein the molecular weight of said carboxylic acid amide is over 46 and $R_1$, $R_2$ and $R_3$ have the above-assigned meanings at a temperature of from 0° to 75°C, subjecting the resultant reaction product to hydrolysis, and recovering said 1-aminoalkane-1,1-diphosphonates.

While the phosphorus trihalide may be $PBr_3$, $PCl_3$ is preferably used as the phosphorus trihalide. It has been found expedient to use the phosphorus trihalide with the carboxylic acid amide in a molar ratio of 3:1, to 1:1 preferably 1:1.

The reaction can be carried out in the absence or in the presence of organic solvents, especially ethers and chlorinated hydrocarbons. The reaction suitably takes place at temperatures of from 0° to 75°C, preferably 45° to 65°C. For carrying out the reaction, it is simply necessary to mix the starting components, possibly with use of an organic solvent, and the phosphorus trihalide is generally added to the monocarboxylic acid amide. It is generally expedient to leave or maintain the temperatuRe of the reaction mixture for some time such as from 10 minutes to 8 hours, within the given temperature range before effecting the subsequent hydrolysis.

The hydrolysis of the reaction mixture may be carried out in the simplest manner by addition of a corresponding amount of water. It can also be produced however, by addition of aqueous acids, as for example, hydrochloric or acetic acids. If desired, it is also possible to hydrolyze the reaction product with aqueous alkaline solutions such as caustic soda, caustic potash or soda solution. In this case, instead of the acids, the corresponding alkali metal salts are first obtained, which if desired can be reconverted into the acids.

The aminoalkane-1,1-diphosphonic acids can be obtained from the reaction mixture, after addition of the hydrolyzing means, by concentration of the solution and cooling or by precipitation with suitable organic solvents, which are miscible with water. In particular, acetone, lower alcohols or mixtures of acetone and ethyl acetate may be used as the organic solvents. It is often possible, however, to use the hydrolyzate obtained directly as a technical product. In such cases it is advantageous to carry out the hydrolysis with water while simultaneously passing through steam, whereby volatile components such as HCl or HBr are driven out by steam distillation.

A special embodiment of the process consists in the reaction of phosphorus trihalides with the monocarboxylic acid amides with simultaneous addition of phosphorous acid. A molar ratio of phosphorus trihalide to phosphorous acid of about 1:1 has been found suitable. The yields of 1-aminoalkane-1,1-diphosphonic acid could be increased in several cases by this method. The phosphorous acid apparently participates in the reaction, since in some cases yields over 100%, based on $PCl_3$ (see Examples 7 and 12 for example) are obtained.

Instead of phosphorous acid and $PCl_3$, it is also possible to use a reaction product of $PCl_3$, with water, when the quantities are calculated so that theoretically a mixture of $PCl_3$ and $H_3PO_3$ is present in the molar ratio of 1:1.

If the corresponding salts are not already obtained directly, as in the case of an alkaline hydrolysis, the 1-aminoalkane-1,1-diphosphonic acids obtained can be converted into the respective salts desired by addition of equivalent amount of corresponding bases. In detail, a stepwise or complete neutralization of the phosphonic acid group can thereby be effected. The water-soluble salts such as alkali metal or ammonium salts are of special interest. These may be prepared by reacting the phosphonic acids with KOH, NaOH, $K_2CO_3$, $Na_2CO_3$ or ammonia. The corresponding mono-, di- or tri- or tetra-alkali metal diphosphonates are obtained, depending on the amounts used. Further, the 1-aminoalkane-1,1-diphosphonic acids form salts with amine bases. Suitable amine bases are mono-, di- or tri-alkanolamines, especially those having a carbon chain length of 1 to 4 carbon atoms, as well as pyridine and guanidine. The reaction for the production of the salts is effected by known methods.

It is possible by the method described to prepare in a simple way 1-aminoalkane-1, 1-diphosphonic acids, in which the amino group is possibly substituted, or their salts. Some of the compounds described are new. In general they possess good complex-forming properties and can be used in many fields of industry, especially for water-softening and as builders for washing compositions.

Mixtures with other complex-forming substances, such as aminotriacetic acid, polyaminopolycarboxylic acids and condensed phosphates, may also be advantageous, in which case the said substances may be employed singly or in admixture.

The present invention will be further described by way of reference to the following specific examples. These, however, are not to be deemed limitative in any manner.

EXAMPLE I 73.1 parts of dimethyl formamide were reacted with 137.3 parts of phosphorus trichloride at 50°C to 70°C. This reaction mixture was maintained at 70°C for about an hour, and then 180 parts of water were slowly added. This solution was treated with acetone in the hot and N,N-dimethyl-1-aminomethane-1,1-diphosphonic acid was precipitated as a crystalline substance in the form of the monohydrate. By further drying at 110°C and 0.1 mm Hg over $P_2O_5$, the compound obtained was converted into the anhydrous diphosphonic acid.

| Loss on drying: | Calculated: | 7.6% |
|---|---|---|
| | Found: | 7.7% |

Analysis of the anhydrous product:

| Calculated: | C = 16.45% | FOUND: | C = 16.75% |
|---|---|---|---|
| | H = 5.06% | | H = 4.89% |
| | N = 6.39% | | N = 6.20% |
| | P = 28.28% | | P = 27.96% |
| Molecular weight: | Calculated: | 219 | |
| | Found: | 218 | |

The yield amounted to 70%, based on the amount of phosphorus trichloride.

EXAMPLE II 73.1 parts of dimethyl formamide were mixed with 41 parts by phosphorous acid and this mixture was reacted with 137.3 parts of phosphorus trichloride at about 70°C. A viscous mass was formed, which after about an hour was treated with 180 parts of water. The solution so obtained was filtered and treated with acetone. A precipitate was formed which was further treated as described in Example 1. N,N-dimethyl-1-aminomethane-1,1-diphosphonic acid was obtained in a yield of 76%, based on $PCl_3$.

EXAMPLE III 73.1 parts of dimethyl formamide were dissolved in 250 parts of carbon tetrachloride and reacted with 271 parts of phosphorus tribromide at about 45°C. A solid mass was formed in the reaction mixture, which was separated and mixed with 180 parts of water. A precipitate was obtained by addition of acetone to the aqueous solution which was worked up, as described in Example I. N,N-dimethyl-1-aminomethane-1,1-diphosphonic acid was obtained in 22% yield.

EXAMPLE IV 73.1 parts of dimethyl formamide were dissolved in 200 parts of dioxan and reacted with 137.3 parts of phosphorus trichloride at 50° to 70°C. 180 parts of water were added to this solution and then the reaction mixture was treated with acetone. The crystalline substance obtained was worked up as in Example I. N,N-dimethyl-1-aminomethane-1,1-diphosphonic acid was obtained in a yield of 66%.

EXAMPLE V 73.1 parts of dimethyl formamide were reacted with 274.6 parts of phosphorus trichloride while cooling with ice. The mixture was allowed to stand for about an hour and was then hydrolyzed with 180 parts of water. The N,N-dimethyl-1-aminomethane-1,1-diphosphonic acid was obtained from the solution so produced by addition of acetone. The yield amounted to 25%.

EXAMPLE VI 73.1 parts of dimethyl formamide were reacted with 137.3 parts of phosphorus trichloride at about 50°C. 150 parts of concentrated hydrochloric acid were added to the reaction mixture and it was then treated with acetone, and the crystalline precipitate obtained is worked up as in Example I. N,N-dimethyl-1-aminomethane-1,1-diphosphonic acid was obtained in 46% yield.

EXAMPLE VII 73.1 parts of dimethyl formamide and 82 parts of phosphorous acid were reacted with 137.3 parts of phosphorus trichloride at 50° to 70°C. The viscous-to-solid reaction mixture formed was, after some time, reacted with 200 parts of water, filtered and precipitated with acetone. The precipitate formed was further treated as described above. A yield of N,N-dimethyl-1-aminomethane-1,1-diphosphonic acid of 132%, based on $PCl_3$, and 66%, based on the total amount of phosphorus was obtained.

EXAMPLE VIII 87 parts of N,N-dimethylacetamide and 250 parts of dioxan were reacted with 434 parts of phosphorus tribromide at about 30°C. The reaction mixture was maintained at 50° to 60° for about 2 hours and was then reacted with 30 parts of water. After 8 to 10 hours two phases formed, the upper phase of which was separated and treated with a further 100 parts of water. This solution was heated at 100°C for 2 to 3 hours. It again formed two phases, the upper of which was separated and treated in the hot with acetone. The oil which thereupon precipitated was dissolved in water and again treated in the hot with acetone. A crystalline precipitate was formed which was filtered off by suction, washed with acetone and dried in the air. The product was the monohydrate of N,N-dimethyl-1-aminoethane-1,1-diphosphonic acid. The product was dried at 110°C and 0.1 mm Hg over $P_2O_5$ and was obtained in the anhydrous form.

| Loss on drying: | Calculated: | 8.25% | | |
|---|---|---|---|---|
| | Found: | 8.10% | | |
| Analysis of the dry product: | | | | |
| Calculated: | C = 20.61% | Found: | C = 20.15% | |
| | H = 5.62% | | H = 5.20% | |
| | N = 6.01% | | N = 5.92% | |
| | P = 26.57% | | P = 25.93% | |
| Molecular weight: | Calculated | 233 | | |
| | Found: | 233 | | |

The yield amounted to 13%, based on $PBr_3$.

EXAMPLE IX 44 parts of butyramide were reacted with 137.3 parts of phosphorus trichloride and heated at 75°C to 80°C for 5 to 6 houurs. Unreacted phosphorus trichloride was removed under vacuo and the residue was reacted with 100 parts of water. It was then treated with sufficient water for practically all to be dissolved and then filtered. When the condensate after a water-bath distillation no longer had an acid reaction, the solution was passed over an acid ion exchanger and concentrated. A precipitate of 1-amino-butane-1,1-diphosphonic acid was obtained from this hot solution by addition of acetone, and is separated and dried.

| Molecular weight: | Calculated: | 233 | |
|---|---|---|---|
| | Found: | 233 | |
| Analysis: | | | |
| Calculated: | C = 20.60% | Found: | C = 20.59% |
| | H = 5.62% | | H = 5.20% |
| | N = 6.00% | | N = 5.89% |
| | P = 26.57% | | P = 26.15% |

EXAMPLE X 120 parts of benzamide were suspended in 300 parts of dioxan and reacted with 541 parts of phosphorus tribromide. Then 82 parts of phosphorous acid dissolved in dioxan were added at about 20°C, and the mixture was heated at 60° to 70° C for 3 to 4 hours. The reaction mixture was poured on ice and then concentrated. Subsequently, the mixture was extracted with acetone and then with ether. The residue was isolated, dissolved in water and precipitated again with ethyl acetate/acetone. The precipitate, the trihydrate of 1-phenyl-1-aminomethane-1,1-diphosphonic acid was isolated and dried in air. The yield amounts to 18%, based on $PBr_3$.

| Molecular weight: | Calculated: | 321 | |
|---|---|---|---|
| | Found: | 320 | |
| Analysis: | | | |
| Calculated: | C = 26.15% | Found: | C = 26.85% |
| | H = 5.34% | | H = 5.08% |
| | N = 4.36% | | N = 4.10% |
| | P = 19.30% | | P = 18.94% |

Drying at 110°C and 0.1 mm Hg over $P_2O_5$ led to the anhydrous compound.

| Loss on Drying: | Calculated: | 16.8% |
|---|---|---|
| | Found: | 16.0% |

EXAMPLE XI 73 parts of N-methylacetamide and 82 parts of phosphorous acid were reacted with 137.3 parts of phosphorus trichloride at about 70°C and the mixture was then maintained at 70°C for a further 8 to 10 hours. It was subsequently filtered hot, the residue was extracted with water, and the united aqueous solutions after concentration were precipitated with acetone. The precipitate, N-methyl-N-aminoethane-1,1-diphosphonic acid, was isolated and dried. A yield of 94% based on $PCl_3$, or 47%, based on the total phosphorus was obtained.

| Molecular weight: | Calculated: | 219 | |
|---|---|---|---|
| | Found: | 218 | |
| Analysis: | | | |
| Calculated: | C = 16.45% | Found: | C = 16.23% |
| | H = 5.06% | | H = 4.91% |
| | N = 6.39% | | N = 6.33% |
| | P = 28.27% | | P = 27.85% |

EXAMPLE XII 50.5 parts of N-butylformamide and 41 parts of phosphorous acid were reacted with 68.5 parts of phosphorus trichloride at about 70°C, and maintained at this temperature for about 4.5 hours. The product was then treated with sufficient water to dissolve practically all. The solution obtained was treated with acetone and the precipitate obtained was isolated. N-butyl-1-aminomethane-1,1-diphosphonic acid was obtained in a yield of 110%, based on $PCl_3$, or 55% based on the total phosphorus.

| Molecular weight: | Calculated: | 247 | | |
|---|---|---|---|---|
| | Found: | 245 | | |
| Analysis: | | | | |
| Calculated: | C = 24.30% | Found: | C = 24.22% | |
| | H = 6.12% | | H = 6.02% | |
| | N = 5.67% | | N = 5.70% | |
| | P = 25.07% | | P = 24.68% | |

EXAMPLE XIII 59 parts of N-methylformamide and 82 parts of phosphorous acid were reacted with 137.3 parts of phosphorus trichloride at about 60°C, and maintained for 2 hours at this temperature. Then 60 parts of water were added to the reaction mixture. The solution was evaporated. The residue was taken up with a little water and treated in the hot with acetone. The crystalline precipitate so formed was isolated and consisted of N-methyl-1-aminomethane-1,1-diphosphonic acid. The yield amounted to 66%, based on $PCl_3$, or 33% based on the total phosphorus.

| Molecular Weight: | Calculated: | 205 | | |
|---|---|---|---|---|
| | Found: | 208 | | |
| Analysis: | | | | |
| Calculated: | C = 11.72% | Found: | C = 11.83% | |
| | H = 4.42% | | H = 4.07% | |
| | N = 6.83% | | N = 6.63% | |
| | P = 30.22% | | P = 30.11% | |

EXAMPLE XIV 127.2 parts of N-cyclohexylformamide and 81 parts of phosphorous acid were reacted with 137.3 parts of phosphorus trichloride at 70°C, and maintained for 5 hours at this temperature. The reaction product was dissolved in water, treated with acetone and the precipitate separated. A 25% yield of N-cyclohexyl-1-aminomethane-1,1-diphosphonic acid, based on $PCl_3$, was obtained.

| Molecular weight: | Calculated: | 273 | | |
|---|---|---|---|---|
| | Found: | 270 | | |
| Analysis: | | | | |
| Calculated: | C = 30.78% | Found: | C = 31.09% | |
| | H = 6.24% | | H = 6.40% | |
| | N = 5.13% | | N = 5.21% | |
| | P = 22.68% | | P = 22.48% | |

EXAMPLE XV 101.1 parts of N,N-diethylformamide and 82 parts of phosphorous acid were reacted with 137.3 parts of phosphorus trichloride at about 70°C and maintained at this temperature for 2 hours. Excess $PCl_3$ was removed from the reaction mass under vacuo and then the residue was treated with 180 parts of water. The solution was subjected to a steam distillation until the condensate no longer showed an acid reaction. Two-thirds of the solution were used as an additive for a liquid cleaning composition. A third of the solution was passed over an acid ion exchanger, concentrated and treated with acetone. The precipitate obtained was isolated and dried. The yield of N,N-diethyl-1-aminomethane-1,1-diphosphonic acid amounted to 91%, based on $PCl_3$ or 45.5%, based on the total phosphorus.

| Molecular weight: | Calculated: | 247 | | |
|---|---|---|---|---|
| | Found: | 248 | | |
| Analysis: | | | | |
| Calculated: | C = 24.30% | Found: | C = 24.77% | |
| | H = 6.12% | | H = 6.07% | |
| | N = 5.67% | | N = 5.58% | |
| | P = 25.07% | | P = 24.87% | |

EXAMPLE XVI 73.6 parts of N-N-dibutylformamide and 41 parts of phosphorous acid were reacted with 68 parts of phosphorus trichloride at 50°C and maintained for 3 hours at this temperature. The product was then treated with 30 parts of water and the reaction mixture was subjected to a steam reaction. The solution was then passed over an acid ion exchanger and concentrated. N,N-butyl-1-aminomethane-1,1-diphosphonic acid was obtained as the crystalline reaction product by treatment with acetone. The yield amounted to 68%, based on $PCl_3$ or 34%, based on the total phosphorus.

| Molecular weight: | calculated: | 302 | | |
|---|---|---|---|---|
| | found: | 306 | | |
| Analysis: | | | | |
| Calculated: | C = 35.65% | Found: | C = 35.69% | |
| | H = 7.65% | | H = 7.52% | |
| | N = 4.62% | | N = 4.56% | |
| | P = 20.43% | | P = 20.48% | |

EXAMPLE XVII 92.7 parts of N-decylformamide and 41 parts of phosphorous acid were reacted with 68.5 parts of phosphorus trichloride at 70°C and the mixture maintained at this temperature for about 5 hours. The reaction mixture was then hydrolyzed with water, dissolved in caustic soda solution and filtered. The solution was then acidified, whereby N-decyl-1-aminomethane-1,1-diphosphonic acid was precipitated. The yield amounted to 60%, based on $PCl_3$.

| Molecular weight: | Calculated: | 331 | | |
|---|---|---|---|---|
| | Found: | 330 | | |
| Analysis: | | | | |
| Calculated: | C = 39.88% | Found: | C = 40.25% | |
| | H = 8.22% | | H = 8.34% | |
| | N = 4.23% | | N = 4.17% | |
| | P = 18.70% | | P = 18.50% | |

EXAMPLE XVIII 68.5 parts of phosphorus trichloride were added to 78.6 parts of N-octylformamide and 41 parts of phosphorous acid at about 70°C and the reaction mixture was maintained at this temperature for 5 hours and then hydrolyzed with 90 parts of water. After addition of further water, the reaction mixture was boiled with active charcoal and filtered. N-Octyl-1-aminomethane-1,1-diphosphonic acid crystallized from the filtrate in the cold and was dried in vacuo over $P_2O_5$. The yield amounts to 48%, based on $PCl_3$.

| Molecular weight: | Calculated: | 303 | | |
|---|---|---|---|---|
| | Found: | 308 | | |
| Analysis: | | | | |
| Calculated: | C = 35.65% | Found: | C = 35.63% | |
| | H = 7.66% | | H = 7.95% | |
| | N = 4.62% | | N = 4.68% | |
| | P = 20.43% | | P = 20.20% | |

EXAMPLE XIX

A mixture of 64.6 parts of N-hexylformamide and 41 parts of phosphorous acid was reacted at about 70°C with 68.5 parts of phosphorus trichloride. After a reaction period of about 5 hours, the product was hydrolyzed with 90 parts of water. After adding further water and active charcoal, the mixture was boiled for a short time and then filtered. The filtrate was treated with acetone and thE precipitated N-hexyl-1-aminomethane-1,1-diphosphonic acid was dried in vacuo over $P_2O_5$. The yield amounted to 94%, based on phosphorus trichloride.

| Molecular weight: | Calculated: | 275 | | |
|---|---|---|---|---|
| | Found: | 273 | | |
| Analysis: | | | | |
| Calculated: | C = 30.55% | Found: | C = 30.50% | |
| | H = 6.96% | | H = 6.59% | |
| | N = 5.09% | | N = 5.07% | |
| | P = 22.51% | | P = 22.10% | |

EXAMPLE XX

With the same method of operation as in Example XIX, but using instead of N-hexylformamide, 57.5 parts of N-3-pentylformamide, N-3-pentyl-1-aminomethane-1,1-diphosphonic acid was obtained in a yield of 62%, based on $PCl_3$, or 45% based on the total phosphorus.

| Molecular weight: | Calculated: | 261 | | |
|---|---|---|---|---|
| | Found: | 260 | | |
| Analysis: | | | | |
| Calculated: | C = 27.595% | Found: | C = 27.43% | |
| | H = 6.561% | | H = 6.38% | |
| | N = 5.364% | | N = 5.30% | |
| | P = 23.721% | | P = 23.67% | |

EXAMPLE XXI 137.2 parts of phosphorus trichloride were added dropwise to a mixture of 135.2 parts of N-benzylformamide and 82 parts of phosphorous acid at 50°C, and the mixture was maintained for 2 hours at this temperature. Then the reaction mixture was slowly treated with 180 parts of water. The solid residue was dissolved in hot water, and the N-benzyl-1-aminomethane-1,1-diphosphonic acid crystallized out in the cold as the monohydrate. The compound obtained was converted into the anhydrous acid by drying at 110°C and 0.1 mm Hg over $P_2O_5$. The yield amounted to 95%, based on $PCl_3$ or 47.5% based on the total phosphorus.

| Molecular weight: | Calculated: | 299 | | |
|---|---|---|---|---|
| | Found: | 295 | | |
| Loss on drying: | Calculated: | 6.0% | | |
| | Found: | 5.8% | | |
| Analysis: | | | | |
| Calculated: | C = 32.12% | Found: | C = 32.58% | |
| | H = 5.054% | | H = 4.64% | |
| | N = 4.682% | | N = 4.75 | |
| | P = 20.708% | | P = 20.32% | |

EXAMPLE XXII

With the same method of operation as described in Example XXI, but using 113.2 parts of N-formylpiperidine instead of N-benzylformamide, piperidinomethane-diphosphonic acid was obtained in a yield of 90% based on $PCl_3$ or 45% based on the total phosphorus.

| Molecular weight: | Calculated: | 259 | | |
|---|---|---|---|---|
| | Found: | 256 | | |
| Analysis: | | | | |
| Calculated: | C = 27.81% | Found: | C = 27.76% | |
| | H = 5.83% | | H = 5.53% | |
| | N = 5.40% | | N = 5.66% | |
| | P = 23.90% | | P = 23.87% | |

EXAMPLE XXIII 67.3 parts of N-dioctyl formamide were reacted with 34.3 parts of phosphorus trichloride at about 60°C and the reaction mixture was maintained at a temperature of 70°C for about 4 hours. Then 400 parts of water were added and after about 4 hours, the precipitated N,N-dioctyl-1-aminomethane-1,1-diphosphonic acid was filtered off and dried. The yield amounted to 70% based on the phosphorus trihalide.

| Molecular weight: | Calculated: | 415 | | |
|---|---|---|---|---|
| | Found: | 416 | | |
| Analysis: | | | | |
| Calculated: | C = 49.14% | Found: | C = 48.96% | |
| | H = 9.46% | | H = 9.52% | |
| | N = 3.37% | | N = 3.29% | |
| | P = 14.91% | | P = 14.51% | |

EXAMPLE XXIV 81.4 parts of didecylformamide and 20.5 parts of phosphorous acid were slowly reacted with 34.3 parts of phosphorus trichloride at 70°C, and the mixture was maintained at 70°C for a further 3 hours. The product was hydrolyzed by the addition of 500 parts of water, the diphosphonic acid thereby being precipitated. This was dissolved in ethanol, precipitated with acetone and dried in vacuo at 50°C. N,N-didecylaminomethane-diphosphonic acid was obtained in a yield of 130% based on $PCl_3$ or 65% based on total phosphorus.

| Molecular weight: | Calculated: | 471 | | |
|---|---|---|---|---|
| | Found: | 468 | | |
| Analysis: | | | | |
| Calculated: | C = 53.48% | Found: | C = 53.81% | |

| | |
|---|---|
| H = 10.04% | H = 9.53% |
| N = 2.97% | N = 3.08% |
| P = 13.13% | P = 12.92% |

EXAMPLE XXV 1 mol of phosphorus trichloride was slowly added to 1 mol of water. The mixture was reacted with 0.5 mol of dimethylformamide and heated at 60°C for about 1 hour. The resulting product was hydrolyzed with water and the N,N-dimethyl-1-aminomethane-1,1-diphosphonic acid was precipitated with acetone. The yield amounts to 44%.

EXAMPLE XXVI 115 parts of N-formylmorpholine and 82 parts of phosphorous acid were mixed and reacted with 137 parts of phosphorus trichloride. The reaction mixture was then treated with about 5000 parts of water, and the solution was filtered and concentrated. The precipitate obtained was isolated and recrystallized from water/acetone. After drying, a yield of 35% of morpholinomethanediphosphonic acid was obtained.

| Molecular weight: | Calculated: | | 261 |
|---|---|---|---|
| | Found: | | 260 |
| Analysis: | | | |
| Calculated: | C = 23.00% | Found: | C = 22.60% |
| | H = 5.02% | | H = 5.18% |
| | N = 5.36% | | N = 5.40% |
| | P = 23.73% | | P = 23.52% |

EXAMPLE XXVII 137 parts of about 90% dioctadecylformamide and 20.5 parts of phosphorous acid were slowly reacted with 34.3 parts of phosphorus trichloride at 70°C and the mixture was maintained for 3 hours at this temperature. At this time, it was hydrolyzed with 500 parts of water. The product was filtered by suction, and the residue was dissolved in alcohol, precipitated again with acetone, isolated and dried in vacuo at 50°C over $P_2O_5$. N,N-dioctadecylaminomethanediphosphonic acid was obtained in a yield of 65%.

| Molecular weight: | Calculated: | | 696 |
|---|---|---|---|
| | Found: | | 685 |
| Analysis: | | | |
| Calculated: | C = 63.85% | Found: | C = 62.88% |
| | H = 11.44% | | H = 12.00% |
| | O = 13.79% | | O = 13.12% |
| | N = 2.01% | | N = 1.98% |
| | P = 8.90% | | P = 8.46% |

EXAMPLE XXVIII

For the preparation of the alkali metal or ammonium salts from the acids, the phosphonic acids according to Examples I to XXVII were dissolved in water, possibly with addition of methanol, and treated with a corresponding amount of alkali metal or ammonium hydroxide in aqueous solution. The amount depended upon how many OH groups of the phosphonic acids are to be neutralized. Accordingly, after drying the reaction mixture in vacuo, the corresponding alkali metal or ammonium diphosphonates were obtained.

EXAMPLE XXIX 1 mol of dimethylformamide is treated with 1 mol of water. This mixture is then slowly dropped into 1 mol of $PCl_3$ at about 60°C. The product was hydrolyzed with at least 2 mols of water, and N,N-dimethyl-1-aminomethane-1,1-diphosphonic acid was precipitated from the hydrolyzate by addition of acetone, giving a yield of 68%, based on $PCl_3$.

If a corresponding amount of dilute caustic soda solution is used for the hydrolysis instead of water, with the same working up, the corresponding sodium salt of N,N-dimethyl-1-aminomethane-1,1-diphosphonic acid was obtained.

EXAMPLE XXX 81.6 parts of N-2,4,6-trimethylphenyl formamide and 41.0 parts of phosphorous acid were reacted with 68.5 parts of phosphorus trichloride at about 70°C. The reaction mixture was maintained at 70°C for about 5 hours and then hydrolyzed with 80 parts of water. The precipitated N-(2,4,6-trimethylphenyl)-aminomethane-1,1-diphosphonic acid was filtered off and washed with acetone to remove unreacted trimethylphenyl formamide. The crude diphosphonic acid was recrystallized from water and dried. The yield amounted to 50% based on $PCl_3$.

| Molecular weight: | Calculated: | | 309 |
|---|---|---|---|
| | Found: | | 309 |
| Analysis: | | | |
| Calculated: | C = 38.85% | Found: | C = 38.79% |
| | H = 5.54% | | H = 5.46% |
| | N = 4.53% | | N = 4.50% |
| | P = 20.03% | | P = 19.98% |

The preceeding specific embodiments are illustrative of the practice of the invention. It is to be understood, however, that other expedients known to those skilled in the art or described herein may be employed without departing from the spirit of the invention or the scope of the appended claims.

We claim:

1. Piperidinomethane-1,1-diphosphonic acid of the formula

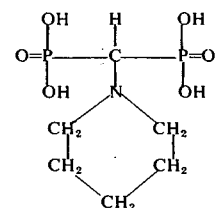

2. Morpholinomethane-1,1-diphosphonic acid of the formula

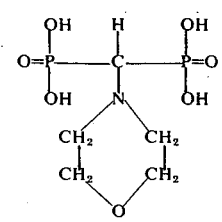

* * * * *